United States Patent [19]
Rodriguez et al.

[11] Patent Number: 5,994,147
[45] Date of Patent: *Nov. 30, 1999

[54] SYSTEM AND METHOD FOR DETERMINING ACID-GAS ($CO_2$, $H_2S$) LOADINGS IN AN ALKANOLAMINE SYSTEM

[75] Inventors: Eduardo F. Rodriguez; Robert R. Craycraft, both of Carthage, Tex.

[73] Assignee: Union Pacific Resources Co., Fort Worth, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/862,779

[22] Filed: May 23, 1997

[51] Int. Cl.⁶ .................................................. G01N 31/16
[52] U.S. Cl. .......................... 436/163; 422/62; 422/75; 436/55; 436/100; 436/102; 436/120; 436/133; 436/139
[58] Field of Search .............................. 436/111–112, 55, 436/163, 133, 120, 139, 100, 102; 422/75–77, 62

[56] References Cited

U.S. PATENT DOCUMENTS

| | | | |
|---|---|---|---|
| 3,844,303 | 10/1974 | Moon et al. | 137/5 |
| 4,031,912 | 6/1977 | Lu et al. | 137/5 |
| 4,033,871 | 7/1977 | Wall | 210/96 |
| 4,172,880 | 10/1979 | Tsavos | 423/210 |
| 4,273,146 | 6/1981 | Johnson | 137/5 |
| 4,277,343 | 7/1981 | Paz | 210/614 |
| 4,323,092 | 4/1982 | Zabel | 137/5 |
| 4,386,058 | 5/1983 | Hass | 423/235 |
| 4,434,033 | 2/1984 | Kaczur et al. | 204/95 |
| 4,465,614 | 8/1984 | Trentham et al. | 423/293 |
| 4,508,602 | 4/1985 | Kaczur et al. | 204/95 |
| 4,844,874 | 7/1989 | deVries | 423/210 |
| 4,877,489 | 10/1989 | Lloyd | 202/181 |
| 4,886,590 | 12/1989 | Tittle | 204/232 |
| 5,162,084 | 11/1992 | Cummings et al. | 210/662 |
| 5,196,345 | 3/1993 | Cooper et al. | 436/55 |
| 5,208,164 | 5/1993 | Cummings | 436/79 |
| 5,364,604 | 11/1994 | Spink et al. | 423/210 |
| 5,398,711 | 3/1995 | Ardrey, Jr. | 137/5 |
| 5,565,180 | 10/1996 | Spink | 423/220 |

Primary Examiner—Jan Ludlow
Attorney, Agent, or Firm—Fulbright & Jaworski; James W. Repass; Ricardo A. Price

[57] ABSTRACT

A method for determining the concentration of acid-gases in an amine-regeneration system, such as is typically found in a natural gas refining plant, having a device for measuring the pH of the system from which the concentration of the acid-gases complexed and the amine can be calculated using an empirically-derived relationship between acid-gas concentration and pH. The invention also includes a system for controlling amine regeneration based upon the above described determining method.

21 Claims, 4 Drawing Sheets

In situ Curve

Any wt% MDEA-DEA SYSTEM

SYSTEM AND METHOD FOR DETERMINING ACID-GAS ($CO_2$, $H_2S$) LOADINGS IN AN ALKANOLAMINE SYSTEM

BACKGROUND OF THE INVENTION

1. Technical Field of the Invention

The present invention relates to the operation and control of an amine-regeneration system, for instance, subsumed within a natural gas refinery plant. More specifically, the invention relates to a method for in situ monitoring of the concentration of acid gases, such as $CO_2$ and $H_2S$, sorbed or complexed to the amine used to remove these acid-gases from natural gas. The method relies upon measuring the pH of the amine stream, whether rich or lean, from which acid-gas loading can be calculated.

2. Description of the Prior Art

Natural gas is a ubiquitous fuel having a variety of applications in both commercial and residential settings. Yet, before natural gas can be used for virtually any application, it must be refined. The most significant refining step is removal of waste or corrosive acid-gases, such as carbon dioxide ($CO_2$), and hydrogen sulfide ($H_2S$). These gases are known in the industry as "acid-gases," because they lower the pH when dissolved in water. For example, hydrogen sulfide is highly toxic, even at trace levels, and therefore must be removed. Carbon dioxide reduces the heating value of natural gas, hence it must also be removed. The primary means by which acid-gases are removed from natural gas is by contact with a suitable base, which reacts with the acid(s) to form a salt. A preferred family of bases in the natural gas refining industry is a family of compounds known as alkanolamines. Alkanolamines are desirable because they react sufficiently well with the acid-gases, yet can be regenerated; that is, the acid-gases can be later removed in a separate step so that the same alkanolamine can be recycled through the system. Other parameters relevant to the selection of a compound for acid-gas removal from natural gas include: (1) loading (e.g., moles $CO_2$/moles reactant); (2) water solubility (the greater the solubility of the base, the more of it that can be used in the system; and (3) low corrosivity. Furthermore, an organic base, such as alkanolamine is preferred because, the organic portion of the amine has a greater affinity for the acid-gases (because of the greater polarity of the amine compared with the natural gas), hence the alkanolamine(s) adsorbs the acid-gases from the natural gas. Examples of typical alkanolamines used in the industry are monoethanol amine, diglycolamine, diethanolamine, diisopropanolamine, triethanolamine, and N-methyldiethanolamine. Finally, it should be noted that one recent trend in the industry is to select compounds which rather than "react" with the acid-gas, simply remove the acid-gases from the natural gas by relying upon the solvents' greater affinity for the acid-gases. Selexol and Rectisol are suitable exemplars of such physical solvents. "Mixed" solvents—i.e., solvents that rely both upon physical adsorption and chemical reaction to remove acid-gases—are also utilized.

Naturally, the capacity of a given quantity of amine to remove acid-gases from natural gas is limited. The quantity of acid-gas adsorbed onto a given quantity of amine is referred to as the "acid-gas loading," and represents the moles of acid-gas removed per mole of amine. In most systems currently practiced, the amine stream is continuously cycled through the system. Here, after loading, the amine must be regenerated—i.e., the acid-gases must be removed from amine (called "stripping"), so that the amine can be recirculated within the system. While the goal of the regeneration process is to remove completely the adsorbed acid-gases, the stripping process is incomplete, which means that the acid-gases are not completely removed from the amine. This, of course, reduces the efficiency of the amine (on a per-unit-of-amine basis) to remove acid-gases from the natural gas. Hence, in order to maximize the efficiency of the removal of acid-gases from the natural gas, the amine-regeneration process must be as effective as possible, i.e., it must return as much "lean" amine upstream where it contacts the natural gas, as possible. To accomplish this, the process variables that control acid-gas stripping from the amine stream must constantly be readjusted. Before this can be accomplished, the system operator must know the concentration of $CO_2$ adsorbed by the amine (the "acid-gas loading") at various points in the system, particularly at the point at which the regenerated amine is returned upstream to react with the natural gas.

Most of the currently available methods for monitoring acid-gas loading are quite old—they involve traditional wet-chemistry techniques well known in the chemical art. Essentially, an aliquot of amine solution is obtained from the system. This aliquot is added to a solution of predetermined pH. This solution is then titrated until the pH returns to the predetermined pH. From the concentration and volume of the titrant needed to restore the pH, the concentrations of $CO_2$ and $H_2S$, and their respective species, can be readily calculated.

This method is overwhelmed with difficulties. For one thing, it is expensive and time-consuming. A laboratory technician must collect the samples, and then perform the analyses in a laboratory. Besides the possibility of human error since the acid-gas loading must be determined manually (i.e., by titration), and besides the accumulation of hazardous wastes (e.g., potassium hydroxide and organic amines), which must be disposed of, there are other more significant reasons that these measurements may lack reliability. Measurements obtained by this way are static measurements, at best; they can be performed only periodically, or intermittently. This is highly problematic since a typical natural gas refining/amine-regeneration system is quite often not in equilibrium, due the constant addition of amine, water, etc. which causes "slug flow" in the system, or points of local disequilibria within the system. Hence what is needed is a method for the in situ monitoring of concentrations of acid gases, and which will allow continuous, real-time monitoring of acid-gas loading. Unfortunately, no such method exists to quickly and accurately measure dissolved gases in a dynamic system that would be suitable for use in a natural gas refining/amine-regeneration system. Dissolved gases are notoriously difficult to measure, particularly so in a system under pressure.

Hence the instant invention is directed towards such an in situ process for determining acid-gas loading by indirect measurement of another more easily determined solution parameter, which then acts as a proxy for acid-gas loading. Other systems are known in the art for determining some desired parameter by direct measurement of a different parameter. U.S. Pat. Nos. 5,208,164 and 5,162,084, issued to Cummings and Cummings et al., respectively, are directed to a process for determining the concentration of various anions (e.g., $SCN^-$, $Cl^-$, $HCO_2^-$) in an alkanolamine solution, by directly measuring electrical conductivity. Similarly, U.S. Pat. Nos. 5,196,345 and 4,273,146, issued to Cooper et al. and Johnson, respectively, measure pH and electrical conductivity to infer the concentration of acidic metal hydrides present in organic liquids, and the concentrations of various salts (e.g., NaCl), respectively. U.S. Pat. No. 4,323,092 issued to Zabel discloses a method to determine free chloride ion ("Cl$^-$") concentration by measuring total dissolved chlorine. U.S. Pat. Nos. 4,172,880 and 3,844,303, issued to Tzavos and Moon et al., respectively, disclose processes in which electrical conductivity is measured to infer total acidity and alkalinity, respectively. U.S. Pat. No. 4,277,343, issued to Paz discloses a method for determining alkalinity by measuring the partial pressure of $CO_2$. U.S. Pat. No. 4,877,489, issued to Lloyd discloses a system for measuring electrical conductivity, and from these values the level of entrained bubbles is determined. Finally, U.S. Pat. No. 5,398,711, issued to Ardrey, Jr. discloses a general method for measuring various solution parameters such as conductivity or pH, and from those, inferring levels of the same or other solution components for the purpose of determining if a corrective response is needed.

SUMMARY OF THE INVENTION

Accordingly one object of this invention is to provide an in situ method for determining dissolved acid-gas concentrations in an aqueous alkanolamine stream.

Another object of this invention is to provide an in situ method for determining dissolved acid-gas concentrations in aqueous alkanolamine streams utilized in amine-regeneration units in engagement with natural gas refining plants.

Yet another object of this invention is to provide a continuous, in situ system for determining acid-gas concentrations in an aqueous alkanolamine stream.

Yet another object of this invention is provide a system for the in situ monitoring of acid-gas loadings in an aqueous alkanolamine stream, determining whether a remedial response is appropriate, then if so, initiating the response.

In accordance with one aspect of the present invention, there is provided a method for the in situ monitoring of acid-gas loading in an amine-containing aqueous stream which comprises the steps of contacting the acid-gas containing aqueous stream by at least one probe operatively engaged with a device for determining the pH of said acid-gas containing aqueous stream, periodically measuring the pH of the stream by interrogating the pH determining device, and finally determining the acid-gas loading of the stream by converting the determined pH to an acid-gas loading value. In one preferred embodiment, at least two probes are utilized, wherein one probe is located upstream from the amine-regeneration unit, and another probe, downstream from the amine-regeneration unit. Hence, one probe is measuring the pH of a rich amine stream, the other, of a lean stream. In another preferred embodiment, the acid-gas loading is determined by means of an algorithm for conversion of pH to acid-gas loading. In yet another preferred embodiment, the determining step comprises a non-linear conversion, which in another embodiment comprises a table of pH-acid gas loading data pairs.

In a particularly preferred embodiment, the pH probes are permanently inserted into the aqueous amine stream. In another embodiment, they may be intermittently placed in the stream. The probe is preferably an electrical probe which obtains the pH by correlation with electrical conductance of the stream. Preferably, the acid-gas loading value is displayed to the operator. In another preferred embodiment, the acid-gas loading value is compared with a pre-determined value, either manually or automatically, and if the difference between the two lies beyond a pre-set limit then a corrective response is initiated so that the acid-gas concentration is brought to with the operating specifications of the plant.

In another aspect of the invention, a method for removing acid gas from an acid-gas containing natural gas stream is provided, which comprises the steps of contacting an acid-gas containing natural gas stream with a lean aqueous amine stream, wherein the amine stream removes a majority of the acid-gas from the natural gas stream, thus forming a rich aqueous amine stream; and the additional step of regenerating the rich amine stream to remove the acid gas and to reform the lean aqueous stream; and providing the lean aqueous amine stream for the contacting step, and the final step of continuously monitoring the loading of the acid gas to determine an acid-gas loading value. In one particularly preferred embodiment, the acid-gas concentrations are determined for both lean and rich amine. In other preferred embodiments, the acid-gas loading is measured on either the rich or the lean side of the system. In another particularly preferred embodiment, the acid-gas loading values are displayed.

In yet another aspect of this invention, a system for in situ monitoring and controlling acid-gas loading of an amine containing aqueous stream is provided, which comprises the steps of contacting the acid-gas containing aqueous stream by at least one probe operatively engaged with a device for determining the pH of said acid-gas containing aqueous stream, periodically measuring the pH of the stream by interrogating the pH determining device, determining the acid-gas loading of the stream by converting the determined pH to an acid-gas loading value, followed by comparing the acid-gas loading value to a pre-determined value, then initiating an appropriate control response if the difference between two said values is greater than a pre-set limit. In preferred embodiments of the present invention, the remedial response is, for instance, increasing the temperature inside the amine still, or increasing the amine strength in the amine stream.

This invention has numerous advantages over the current state-of-the-art. Most of these advantages flow from the continuous in situ measurement of the relevant parameter, rather than periodic and intermittent bench measurement. For purposes of the present invention, "in situ," refers to measurements made by inserting the probe directly into the amine stream any one or more points in the system. Thus, in situ measuring has the capability to provide real-time, continuous measurements. Yet in situ measurements are not limited to continuous, real-time measurements, but instead may provide intermittent measurements, and measurements that may also be stored rather than processed immediately. For instance, unlike the currently available systems for determining acid-gas loading in amine containing streams, no reagents or laboratory instruments other than a pH meter are needed. Because of this there are no chemical wastes to be disposed of, nor need a laboratory technician be employed to collect the data, nor is the quality of the data diminished by human error. In addition to human error, there is intrinsic error associated with measuring any stream parameter by taking a sample from the system rather than measuring in situ.

The present invention relates to a method for measuring acid gases in solution. Dissolved gases will evaporate into the head-space, or "out-gas" if the system pressure is reduced—for instance, if a closed system under pressure is immediately opened to the atmosphere. In the case of an amine-regeneration system, the majority of the system is operated under pressure greater than 1 atmosphere. Thus, when a sample is taken from the system and exposed to normal atmospheric pressure, e.g., in the laboratory where the measurements are carried out, out-gassing will occur, that is, the acid gases will leave the solution. Therefore, lower concentrations of acid gas are likely to result from grab samples compared with in situ sampling. Therefore, the determination of acid-gas loading arrived at by the present invention is likely to be more precise and more accurate, hence more reliable than measurements obtained by the currently available method. In addition, if automated, the present invention allows the determination of acid-gas loading to be tied in with the control system. Furthermore, in situ monitoring, which is the only means to provide continuous real-time data—is highly desirable, indeed necessary, in systems of this type. The reason is that such systems are often not at equilibrium, for instance, because of constant additions of various solutes to the system, e.g., slug flow of amine solution from a surge tank or other source is quite common. One consequence of this is that intermittent measurements may not record spikes in the concentrations—i.e., drastic but temporary increases in the chemical composition of the aqueous stream. Furthermore, if amine-regeneration process is perturbed such that it becomes less efficient at regenerating the amine—i.e., it recirculates back into the natural gas refining system, an amine stream unacceptably high in acid-gases—then corrections must be made to the system immediately, for instance, by increasing the fuel gas flow to the reboiler, thereby raising the temperature of the steam delivered to the amine stripper. Yet an effective control response cannot be effected without knowing the amine loading. Therefore, continuous, real-time monitoring is absolutely essential to proper operation of an amine-regeneration system.

The term "acid-gas loading" refers to the concentration of acid gases such as $CO_2$ and $H_2S$, sorbed or complexed to the amine used to remove these acid-gases from natural gas. The term "amine strength" is likewise a chemical attribute of the amine stream and refers to the concentration of amine present in the stream.

BRIEF DESCRIPTION OF THE DRAWINGS

FIG. 1 also shows the placement of acid-gas monitoring devices in a current state-of-the-art system.

DETAILED DESCRIPTION OF THE PREFERRED EMBODIMENTS

Figure 1:
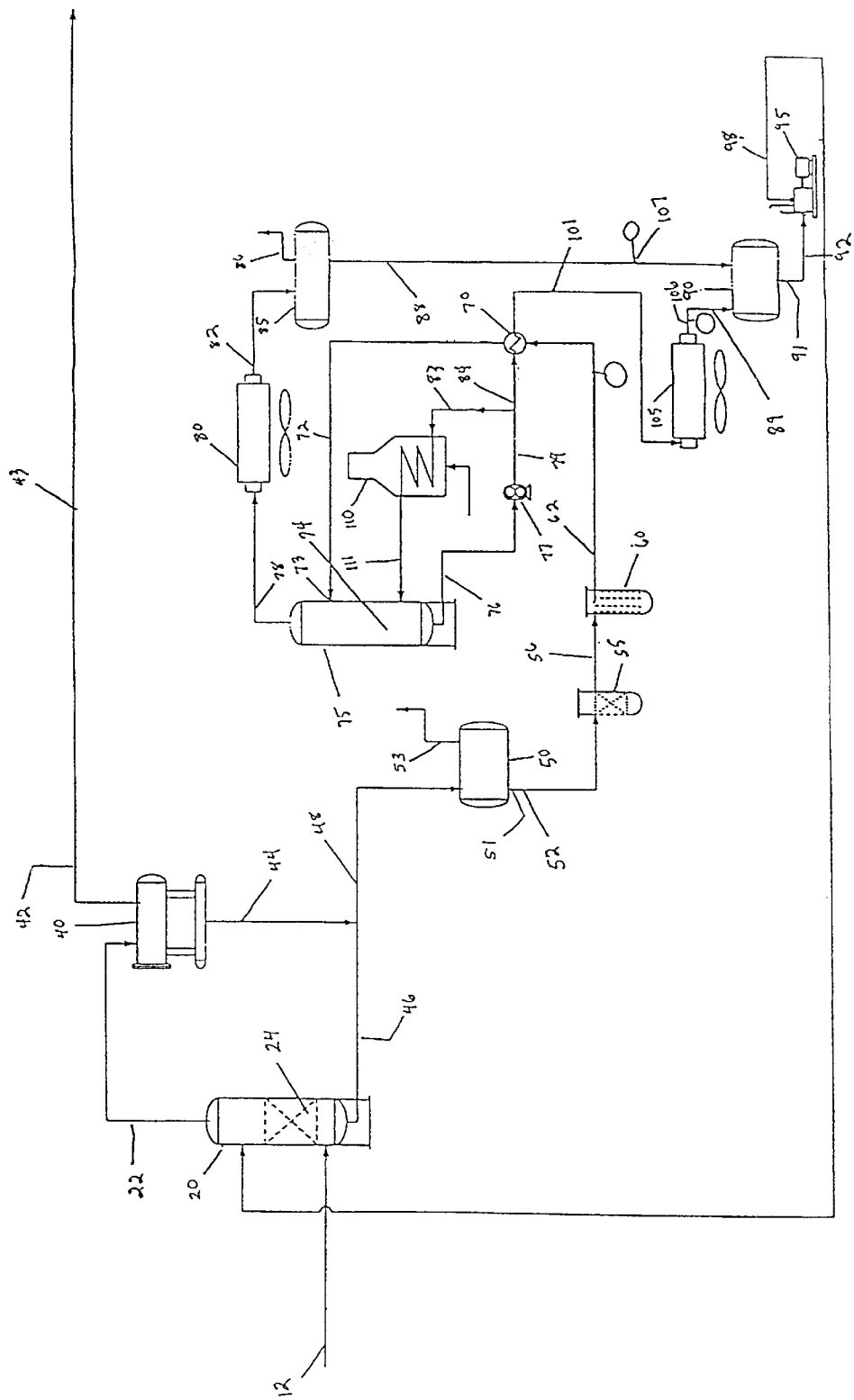
FIG. 1 is a schematic diagram of a natural gas refining plant typical in the industry, and represents a typical operating environment for the present invention.

Depicted in FIG. 1 and described below is a typical gas plant which is comprised of two aspects: one, a system for removing acid-gases from the natural gas utilizing alkanolamine, and two, the system for regenerating the resultant acid-gas rich alkanolamine by removing the acid-gas so that it can be recirculated through the first system. Hence the systems described in FIG. 1 represent a typical environment in which the present invention is preferably utilized.

The natural gas is delivered from a source (not shown) via a conduit 12 to an amine contactor 20. Amine contactors are well known in the industry; for instance, a state-of-the art process is described in U.S. Pat. No. 5,364,604, issued to Spink et al. Typically the natural gas from the source undergoes certain preliminary treatment upstream of the contactor 20. For example, the natural gas may pass through a separator which separates the natural gas from the liquid hydrocarbon and produced water. Then the natural gas typically encounters a particulate filter or "dust filter," which removes particulate matter from the natural gas. After leaving the particulate filter, the natural gas proceeds next to a molecular sieve which further removes water from the natural gas stream. Next, the natural gas moves to a second particulate filter or second "dust filter." The natural gas stream then travels to an amine contactor 20.

Typical operating pressures within the contactor vary between 0 and 1200 psig. The diameter of the contactor varies greatly depending primarily upon the feed-gas flow rate delivered to the contactor. In the amine contactor, "lean" amine—that is, purified amine or acid-gas depleted amine is introduced to the top of the contactor 20 from conduit 98. The lean amine then flows downward in the amine contactor where it encounters the acid-gas rich natural gas flowing upward. As a consequence of this countercurrent contact flow, as the acid-gas rich natural gas flows upward, it is stripped of its acid-gas by the lean amine, thus the natural gas reaching the top of the contactor is substantially free of acid-gas. The present invention is operable without regard to the particular amine contactor utilized in this system. The internal configuration 24 of the amine contactor may consist of a series of bubble trays, packing, or any other material known to the industry which enhances the surface area available for gas-liquid contact. The particular internal configuration depends upon many factors, including the concentration of acid-gases in the feed gas, the ratio of $CO_2$ to $H_2S$, contactor pressure, feed gas temperature, amine temperature, and the $CO_2$ to $H_2S$ levels desired in the end product natural gas.

The now "lean" or substantially acid-gas free natural gas stream exits the top of the contactor via line 22. Although the natural gas stream had been previously dried by contact with a molecular sieve, for example, it is necessarily re-wetted (with water and alkanolamine) in the amine contactor. Therefore, the now "lean" or substantially acid-gas free natural gas stream must undergo a subsequent dehydration, which it does in the coalescer 40. The purpose of the coalescer again, is to separate the amine solution consisting of amine and water from the lean natural gas. The purified natural gas finally exits the coalescer via line 42 and proceeds through a transport line 43 to market. The above description relates to the natural gas refining portion of the system. The remainder of the description of FIG. 1 will focus upon the amine-regeneration portion of the system.

Returning to the amine contactor 20, the amine solution that has been separated in the coalescer 40 exits the coalescer via conduit 44, and converges with acid-gas rich amine which exits the bottom of the amine contactor 20 via a conduit 46. The two conjoined acid-gas rich amine streams proceed via a conduit 48 to an amine flash tank 50. At about this point in the system—a point at which the amine stream is at approximately atmospheric pressure—the current practice in the industry is to sample at sample point 51 (to determine acid-gas loading of the rich amine stream) to reduce out-gassing which will confound the measurement of acid-gas loading (i.e., it will be artificially low). Hence, the current practice is severely limiting to the system operator since the system cannot be reliably queried to determine acid-gas loading at points other than points where the system is close to atmospheric pressure. Returning to the amine flash tank 50, a significant portion of the acid-gas is delivered to a flare via line 53, where the acid-gas is removed from the system—by flashing. The resulting acid-gas depleted amine stream exits the flash tank 50 via conduit 52 and proceeds to an amine cartridge filter 55. The amine cartridge filter contains, preferably an 8–25 micron filter, for final removal of particulates from the amine stream.

The stream next moves via a conduit 56 to an amine charcoal filter 60. In this charcoal filter, organic compounds consisting of hydrocarbon or any other contaminant not removed in the flash tank 50 are removed by adsorption by the charcoal filter 60. Next, the amine stream exits the amine charcoal filter 60 via a conduit 62. The amine stream next proceeds to a lean/rich amine heat exchanger 70. The purpose of this heat exchanger is to preheat the rich amine stream on its way to the amine still 75. Prior to entering the heat exchanger the temperature of the amine is approximately 130° F. The purpose of the heat exchanger at this point in the process is to preheat the amine stream to approximately 190° F. The amine stream is then delivered via a conduit 72 to an amine still (or "stripper") 75 where the $CO_2$-rich amine is stripped of the acid-gas by steam, liberating the acid-gas.

The chemical process occurring inside the stripper is essentially a reversal of the acid-base reaction that occurred within the amine contactor 30. The source of the steam is the regeneration reboiler 110. One internal configuration 74 of the separator preferred in the industry comprises about 20 stripping trays and two to four reflux trays above the feed point 73. At this point, the temperature of this acid-gas depleted amine is approximately 240° F. The acid-gas depleted amine—i.e., lean amine—exits the bottom of the amine still via conduit 76. The conduit 76 delivers the lean amine stream to an amine booster pump 77 to allow further circulation through the amine-purification system.

The stream exits the amine booster pumps via conduit 79, at which point the amine stream is bifurcated into two streams, one stream traveling via a conduit 83, the other via conduit 84. The stream traveling via conduit 83 is delivered to an amine reboiler 110. In the reboiler the amine stream is reheated and delivered via a conduit 111 to the amine still 75. The other stream traveling via a conduit 84 reaches the heat exchanger 70; the amine stream traveling via this conduit is at a temperature of approximately 240°, hence it is used to heat the rich amine stream traveling to the heat exchanger via conduit 62, previously discussed. Next, the lean amine stream originating in conduit 84 exits the heat exchanger via conduit 101 and travels to a lean amine cooler 105 which further cools the lean amine to allow it to enter the natural gas processing system. After cooling in the lean amine cooler 105, the amine stream exits the cooler via a conduit 89 at a temperature of approximately 120° F. Next, the lean amine stream travels to an amine surge tank 90. The purpose of the amine surge tank is to maintain constant flow of the amine solution throughout the system; that is, to act as a reservoir or a surge cushion. As needed, lean amine solution is delivered from the amine surge tank 90 via conduit 92 to an amine circulating pump 95 for delivery to the amine contactor 20 via a conduit 98. At about this point in the system 91, the current practice in the industry contemplates the placement of a second sampling point (to determine loading in the lean amine stream). Again, grab sampling is limited to points in the system where system pressure is at or near atmospheric pressure.

Returning to the amine still 75, again, acid-gas, e.g., $CO_2$, is removed by heat to regenerate the amine. The acid-gas rich steam is carried from the amine still 75 via conduit 78 to an amine still condenser 80. The purpose of the amine still condenser 80 is to condense acid-gas rich steam. The condensed solution in the amine still condenser is delivered via a conduit 82 to an amine still overhead scrubber 85 which separates the condensed solution from the acid-gas. The acid gas leaves the amine still overhead scrubber via a conduit 86. The condensed solution exits the amine still overhead scrubber 85 via a conduit 88 and is delivered to the amine surge tank 90.

Figure 2:
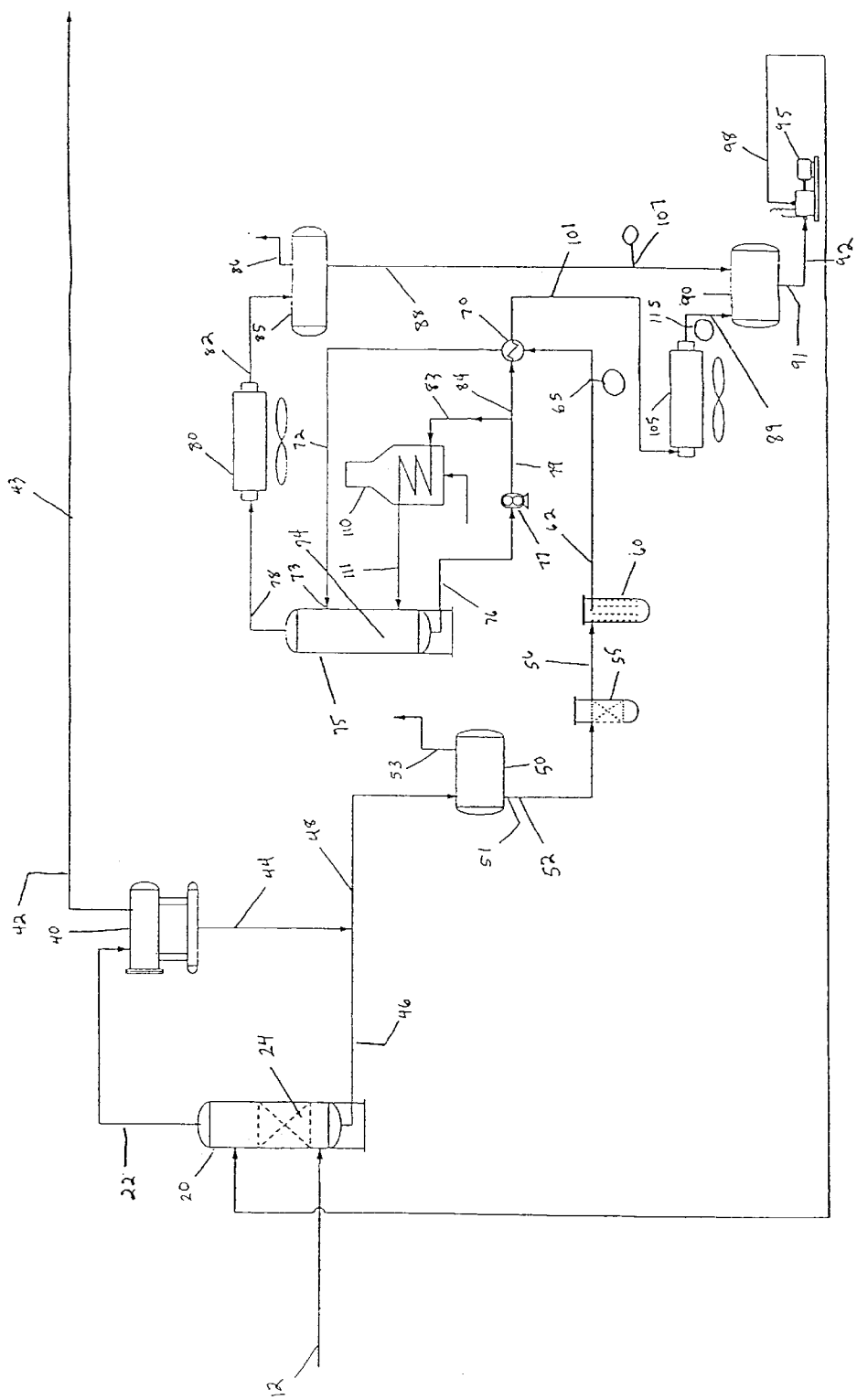
FIG. 2 is the same schematic diagram as shown in FIG. 1, except that FIG. 2 shows a preferred placement of acid-gas monitoring devices of the present invention.

FIG. 2 shows the identical system as that in FIG. 1 except that FIG. 2 additionally depicts one particularly preferred placement of the pH probes of the present invention. The most significant aspect of FIG. 2, when compared with FIG. 1, is that sampling points are not needed; instead, the relevant solution parameter (i.e., acid-gas loading) is determined in situ. The significance of this is that in situ measurements can be performed at any point along the system, not just those points were the system is at or near atmospheric pressure. The reason for this is, again, that since no "sampling is done," which means that an aliquot of the stream is not extracted from the system and exposed to atmospheric pressure, but rather a probe is inserted directly and unobtrusively into the system, the probes can be placed anywhere in the system, which means that acid-gas loading can be determined at any point in the system. FIG. 2 depicts one preferred placement of two pH probes, one to determine acid-gas loading in the rich amine stream 65, the other to determine acid-gas loading in the lean stream 115.

Figure 3:
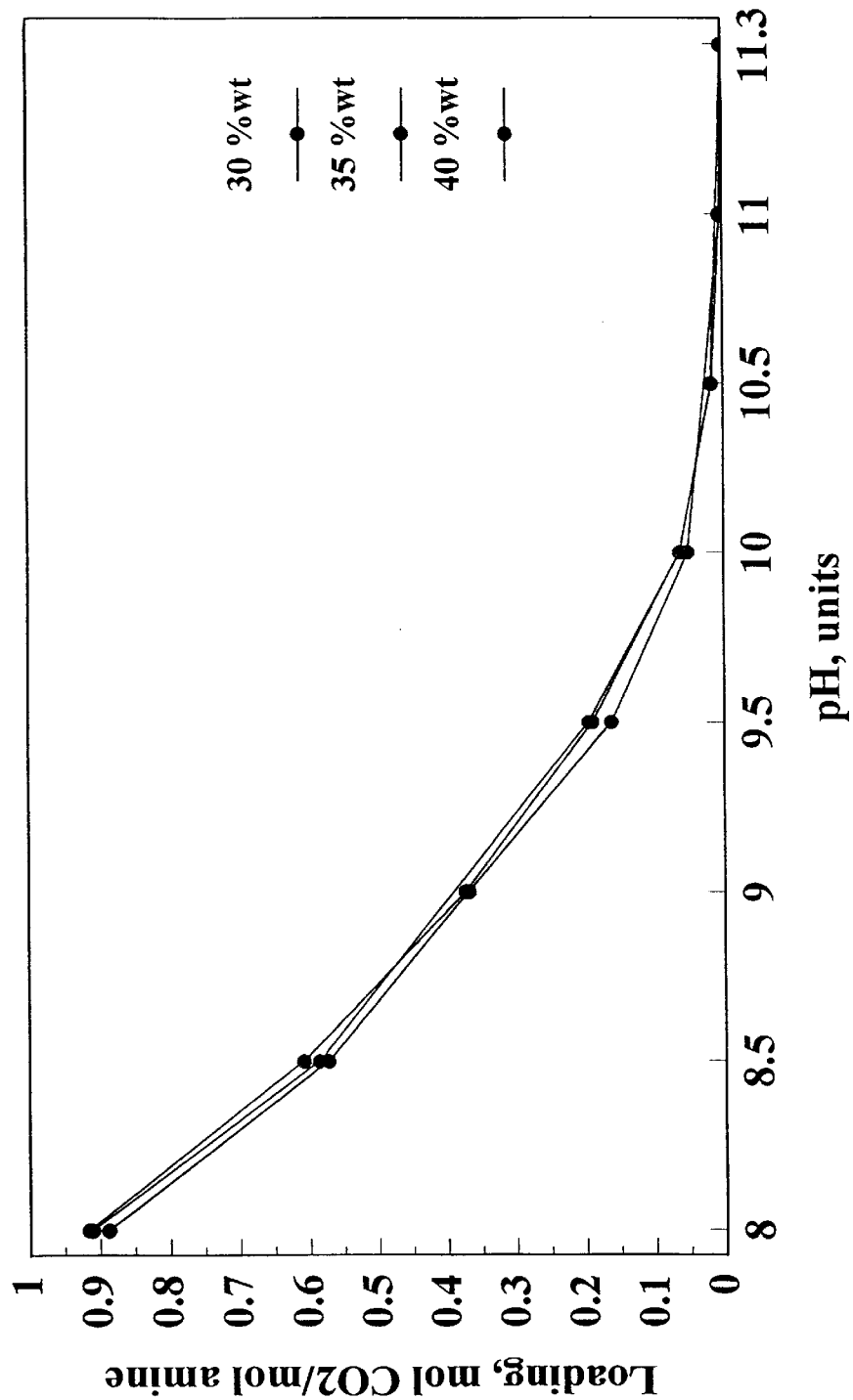
FIG. 3 shows graphically empirical data with pH on the X-axis and acid-gas loading on the Y-axis, for three different amine loadings.
Figure 4:
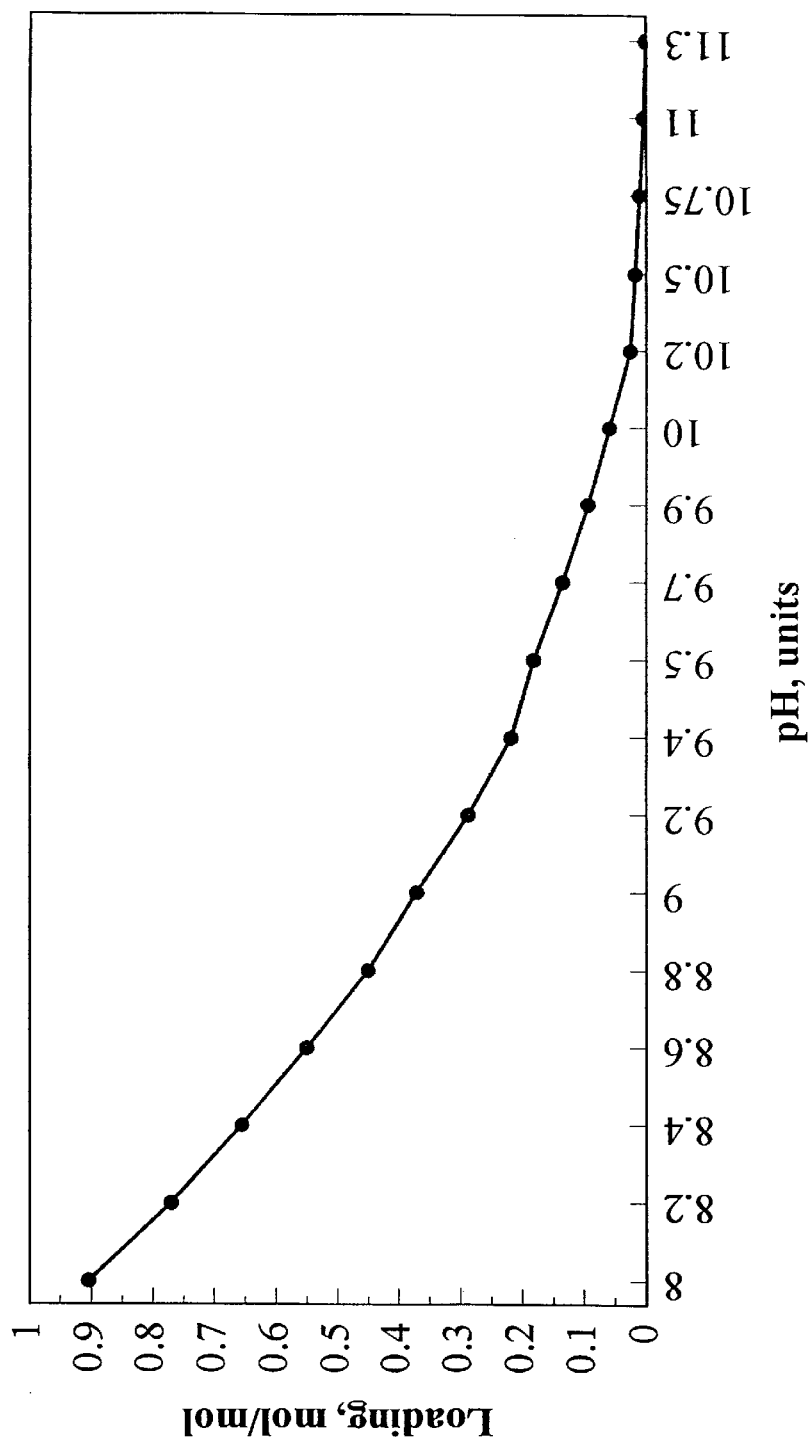
FIG. 4 shows additional empirical data where pH appears on the X-axis and acid-gas loading appears on the Y-axis, for several solutions containing different concentrations of amine.

FIG. 3 shows acid-gas loading (moles $CO_2$/moles amine) as a function of pH for three different amine strengths. The most remarkable feature depicted by this data is the virtual insensitivity of pH to amine concentration, across three different values of amine concentration, 30% (amine by weight), 35%, and 40%. Second, FIG. 3 depicts the experimental data used to infer acid-gas loading from measurement of pH of the amine solution. As depicted by FIG. 3, various concentrations of $CO_2$ are sorbed by the solution of a given amine concentration. For each $CO_2$ loading, the pH is measured, these two values comprise a single data point which is plotted on a graph such as FIG. 3. After pH is measured for several different $CO_2$ loading (in the case of FIG. 3, eight) a curve is fit through the data. The equation describing the curve is then used to calculate acid-gas loading for a given pH measurement, for any amine concentration. FIG. 4 depicts a set of data and fitted curve, similar to those shown in FIG. 3.

The invention thus described may be utilized in a variety of settings. In one preferred embodiment of the present invention, one or more probes for measuring pH are placed in situ, i.e., directly into the amine stream. In one particularly preferred embodiment, one pH probe is placed in the rich amine stream (downstream from the contactor, but upstream from the amine-regeneration unit), and another in the lean amine stream (downstream from the amine-regeneration system). Alternatively, the pH measurements may be made from a hand-held pH meter which is engaged as-needed to a pre-placed in situ probe. Finally, the probes need not be permanent, but rather may be placed at various points in the stream as needed. Measurements of pH may be made on a continuous basis, on a semi-continuous basis, or intermittently. Likewise, the pH measurements may be immediately furnished to the plant operator or may be stored for later reference.

Once made, the pH measurements may be processed in a variety of ways. The present invention is directed towards a method for determining acid-gas loadings in alkanolamine streams using pH measurements. Hence the ultimate endpoint of the measurements is not pH but acid-gas concentration. Therefore, the processing of the pH measurements involves, through a variety of means, conversion of pH to acid-gas concentration. Regardless of the particular embodiment, the conversion relies upon an underlying empirical relationship between pH and acid-gas concentration. Hence, a series of a priori pH measurements must be made at various pre-determined acid-gas loadings, e.g., FIGS. 3 and 4. In one particularly preferred embodiment, one or more curves are numerically fit through the data, and subsequent acid-gas concentrations calculated from pH measurements by inserting the pH value into the equation that numerically best fits the data points. In one particularly preferred embodiment, this process can be converted into an algorithm, the algorithm stored in a processor operatively engaged to the pH meter, such that upon measuring the pH of the amine stream, the acid-gas loading is instantly calculated. In another embodiment, the pH-acid-gas concentration data pairs are tabulated. Hence the operator measures pH then compares that pH with the closest pH value appearing on the table and determines the approximate acid-gas loading by reading the corresponding acid-gas concentration for that pH value. Alternatively, these data may be stored in Read-only memory (ROM) such that the corresponding stored acid-gas loading valves are retrievable from the memory.

In another embodiment of the present invention, the method for determining acid-gas loading may be linked to a control system. Plant specifications dictate the optimum operating conditions, which include the desired acid-gas loadings at various points in the process. Preferably, the control system directs a system operatively engaged to the plant to initiate a remedial response. The control system then, compares the acid-gas loading determined from the pH value measured in situ with the appropriate set of pre-determined acid-gas loadings (i.e., the desired values). Then if the difference between the desired value and the just-determined value lies above a pre-set value, then the system either informs the operator who then manually directs a corrective response, or else the system automatically orders the corrective response. An "appropriate remedial response" comprises a broad spectrum of possible actions taken by the operator. For example, if the amine stream immediately downstream from the contactor has a lower acid-gas concentration that is called for by the specification, and that difference is greater than some pre-set limit, then this may indicate insufficient removal of acid-gases from the natural gas. Therefore, depending upon the precise configuration of the amine contactor, the operator may alter the flow rates of amine or natural gas through the contactor, or increase the concentration of amine in the stream passing through the contactor. Obversely, if it is determined that the acid-gas loading in the lean amine stream is too high, this indicates insufficient removal of acid-gas, which in turn indicates that the amine stream, this time already laden with acid-gas, will not adequately remove acid-gas from the natural gas within the contactor. Therefore, a corrective step is called for within the amine-regeneration system, for instance, the temperature inside the amine still may be increased.

Whereas this invention is illustrated and described in detail with particular reference to presently preferred embodiments of this invention, it should be understood that innumerable changes are possible without departing from the inventive concepts claimed.

What is claimed is:

1. A method for in situ monitoring acid-gas loading of an amine-containing aqueous stream, comprising the steps of:
    contacting an acid-gas containing aqueous amine stream by at least one probe operatively engaged with a device for determining the pH of said acid-gas containing aqueous stream;
    determining the pH of said stream by interrogating said pH determining device; and
    determining the acid-gas loading of said stream by converting said determined pH to an acid-gas loading value by reference to an empirically derived pH to acid-gas loading curve which is independent of amine concentration.

2. The method of claim 1, wherein said determining step comprises contacting a first aqueous amine stream with a first probe and a second aqueous amine stream with a second probe, wherein said first aqueous amine stream has an acid-gas concentration larger than said second aqueous amine stream.

3. The method of claim 1, wherein said determining step comprises utilizing an algorithmic calculation that describes said empirically derived pH to acid-gas loading curve.

4. The method of claim 1, wherein said determining step comprises utilizing a non-linear conversion that describes said empirically derived pH to acid-gas loading curve.

5. The method of claim 4, wherein said non-linear conversion is a look-up table.

6. The method of claim 1, wherein said contacting step comprises permanently immersing said probe in said aqueous amine stream.

7. The method of claim 1, wherein said contacting step comprises intermittently immersing said probe in said aqueous amine stream.

8. The method of claim 1, wherein said probe is an electrical probe and said periodically determining step comprises obtaining a pH reading corresponding to the electrical conductivity of said stream.

9. The method of claim 1, further comprising the step of displaying said determined acid-gas loading value.

10. The method of claim 1, comprising the further step of adjusting the acid-gas concentration of said aqueous stream based upon the determined acid-gas loading value.

11. An in situ method for removing acid-gas from an acid-gas containing natural gas stream, comprising the steps of:
    contacting an acid-gas containing natural gas stream with a lean aqueous amine streams, thus forming a rich aqueous amine stream;
    regenerating said rich amine stream to remove said acid-gas and to reform said lean aqueous amine stream;
    providing said lean aqueous amine stream for said contacting step; and
    monitoring in situ the loading of said acid-gas to determine an acid-gas loading value by reference to an empirically derived pH to acid-gas loading curve which is independent of amine concentration.

12. The method of claim 11, wherein said in situ monitoring step includes continuously monitoring the loading of said acid-gas in both said rich and lean aqueous amine streams.

13. The method of claim 11, wherein said in situ monitoring step includes continuously monitoring said acid-gas loading in said lean aqueous amine stream.

14. The method of claim 11, wherein said in situ monitoring step includes continuously monitoring said acid-gas loading in said rich aqueous amine stream.

15. The method of claim 11, comprising the further step of displaying said acid-gas loading values.

16. The method of according to either claim 1 or claim 11, wherein said empirically derived pH to acid-gas loading curve is composed of multiple line segments connecting the following points:
pH=8.0, Loading, mol/mol=0.91;
pH=8.2, Loading, mol/mol=0.77;
pH=8.4, Loading, mol/mol=0.66;
pH=8.6, Loading, mol/mol=0.55;
pH=8.8, Loading, mol/mol=0.44;
pH=9.0, Loading, mol/mol=0.37;
pH=9.2, Loading, mol/mol=0.29;
pH=9.4, Loading, mol/mol=0.22;
pH=9.5, Loading, mol/mol=0.18;
pH=9.7, Loading, mol/mol=0.14;
pH=9.9, Loading, mol/mol=0.10;
pH=10.0, Loading, mol/mol=0.06;
pH=10.2, Loading, mol/mol=0.03;
pH=10.5, Loading, mol/mol=0.02;
pH=10.75, Loading, mol/mol=0.01;
pH=11.0, Loading, mol/mol=0.005; and
pH=11.3, Loading, mol/mol=0.001.

17. A system for in situ monitoring and controlling acid-gas loading of an amine-containing aqueous stream, comprising the steps of:
contacting an acid-gas containing aqueous amine stream by at least one probe operatively engaged with a device for determining the pH of said acid-gas containing aqueous stream;
determining the pH of said stream by interrogating said pH determining device; and
determining the acid-gas loading of said stream by converting said determined pH to an acid-gas loading value by reference to an empirically derived pH to acid-gas loading curve which is independent of amine concentration;
comparing the acid-gas loading value to a pre-determined value; and
initiating an appropriate remedial response if the difference between the two said values is greater than a pre-set limit.

18. The system of claim 17, wherein said remedial response is changing the temperature inside an amine still.

19. The system of claim 17, wherein the remedial response is changing the amine strength in the amine stream.

20. The system of claim 17, wherein the remedial response is changing amine stream circulation rates.

21. The system according to claim 17, wherein said empirically derived pH to acid-gas loading curve is composed of multiple line segments connecting the following points:
pH=8.0, Loading, mol/mol=0.91;
pH=8.2, Loading, mol/mol=0.77;
pH=8.4, Loading, mol/mol=0.66;
pH=8.6, Loading, mol/mol=0.55;
pH=8.8, Loading, mol/mol=0.44;
pH=9.0, Loading, mol/mol=0.37;
pH=9.2, Loading, mol/mol=0.29;
pH=9.4, Loading, mol/mol=0.22;
pH=9.5, Loading, mol/mol=0.18;
pH=9.7, Loading, mol/mol=0.14;
pH=9.9, Loading, mol/mol=0.10;
pH=10.0, Loading, mol/mol=0.06;
pH=10.2, Loading, mol/mol=0.03;
pH=10.5, Loading, mol/mol=0.02;
pH=10.75, Loading, mol/mol=0.01;
pH=11.0, Loading, mol/mol=0.005; and
pH=11.3, Loading, mol/mol=0.001.

* * * * *